United States Patent
Taniguchi

(10) Patent No.: US 10,156,435 B1
(45) Date of Patent: Dec. 18, 2018

(54) SHAPE MEASURING APPARATUS AND SHAPE MEASURING METHOD

(71) Applicant: Toshiba Memory Corporation, Tokyo (JP)

(72) Inventor: Rikiya Taniguchi, Yokohama Kanagawa (JP)

(73) Assignee: Toshiba Memory Corporation, Tokyo (JP)

( * ) Notice: Subject to any disclaimer, the term of this patent is extended or adjusted under 35 U.S.C. 154(b) by 0 days.

(21) Appl. No.: 15/896,194

(22) Filed: Feb. 14, 2018

(30) Foreign Application Priority Data

Sep. 19, 2017 (JP) ................. 2017-179416

(51) Int. Cl.
| | |
|---|---|
| *G01B 11/24* | (2006.01) |
| *G06F 17/11* | (2006.01) |
| *G01B 15/04* | (2006.01) |
| *G01J 1/44* | (2006.01) |
| *G01B 7/28* | (2006.01) |
| *G01J 1/16* | (2006.01) |

(52) U.S. Cl.
CPC ............... *G01B 11/24* (2013.01); *G01B 7/28* (2013.01); *G01B 15/04* (2013.01); *G01J 1/16* (2013.01); *G01J 1/44* (2013.01); *G06F 17/11* (2013.01)

(58) Field of Classification Search
CPC . G01B 11/25; G01B 11/2513; G01B 11/2509; G01B 11/2527; G06T 7/0057
USPC ....................................................... 356/603
See application file for complete search history.

(56) References Cited

U.S. PATENT DOCUMENTS

| | | | |
|---|---|---|---|
| 9,631,593 B2 | 4/2017 | Nakajima et al. | |
| 2005/0219548 A1* | 10/2005 | Muroya | G01B 11/24 356/504 |
| 2009/0066967 A1* | 3/2009 | Muroya | G01B 11/24 356/504 |
| 2013/0208973 A1 | 8/2013 | Brill | |

(Continued)

FOREIGN PATENT DOCUMENTS

| | | |
|---|---|---|
| JP | 2013-068419 A | 4/2013 |
| JP | 2016-8542 | 1/2016 |
| JP | 2016-118563 | 6/2016 |

(Continued)

*Primary Examiner* — Md M Rahman
(74) *Attorney, Agent, or Firm* — Finnegan, Henderson, Farabow, Garrett & Dunner, L.L.P.

(57) ABSTRACT

In one embodiment, a shape measuring apparatus includes a memory to store, as information regarding a pattern provided in a sample, two-dimensional information regarding a plane parallel with a surface of the sample, and an irradiation module to irradiate the surface of the sample with a beam. The apparatus further includes an irradiation controller to control an irradiation direction of the beam to the sample in accordance with the two-dimensional information, and an acquisition module to acquire scattering intensity data regarding the beam reflected by the surface of the sample. The apparatus further includes a calculator to calculate predicted scattering intensity data regarding the beam in accordance with a shape model that represents a three-dimensional shape of the pattern with a parameter, and a measurement module to measure the three-dimensional shape by adjusting the parameter and fitting the scattering intensity data and the predicted scattering intensity data.

20 Claims, 6 Drawing Sheets

(56) References Cited

U.S. PATENT DOCUMENTS

2016/0035538 A1\* 2/2016 Fukuda ................ H01J 37/285
  250/307
2017/0074647 A1 3/2017 Yamanaka

FOREIGN PATENT DOCUMENTS

JP 2016-217816 A 12/2016
JP 2017-53828 3/2017

\* cited by examiner

SHAPE MEASURING APPARATUS AND SHAPE MEASURING METHOD

CROSS REFERENCE TO RELATED APPLICATION

This application is based upon and claims the benefit of priority from the prior Japanese Patent Application No. 2017-179416, filed on Sep. 19, 2017, the entire contents of which are incorporated herein by reference.

FIELD

Embodiments described herein relate to a shape measuring apparatus and a shape measuring method.

BACKGROUND

Three-dimensional shapes of patterns provided in a sample can be measured by irradiating a sample with a beam, which does not destroy the sample. In this case, the three-dimensional shapes are measured by fitting data acquired by the beam irradiation of the sample and scattering intensity data predicted from shape models of the patterns. However, when the patterns are complicated, the number of parameters of the shape models increases. This causes a problem of an increase of the measurement time and degradation of the measurement accuracy.

DETAILED DESCRIPTION

Embodiments will now be explained with reference to the accompanying drawings.

In one embodiment, a shape measuring apparatus includes a memory configured to store, as information regarding a pattern provided in a sample, two-dimensional information regarding a plane parallel with a surface of the sample, and an irradiation module configured to irradiate the surface of the sample with a beam. The apparatus further includes an irradiation controller configured to control an irradiation direction of the beam to the sample in accordance with the two-dimensional information, and an acquisition module configured to acquire scattering intensity data regarding the beam reflected by the surface of the sample. The apparatus further includes a calculator configured to calculate predicted scattering intensity data regarding the beam in accordance with a shape model that represents a three-dimensional shape of the pattern with use of a parameter, and a measurement module configured to measure the three-dimensional shape of the pattern by adjusting the parameter of the shape model and by fitting the scattering intensity data and the predicted scattering intensity data.

First Embodiment

Figure 1:
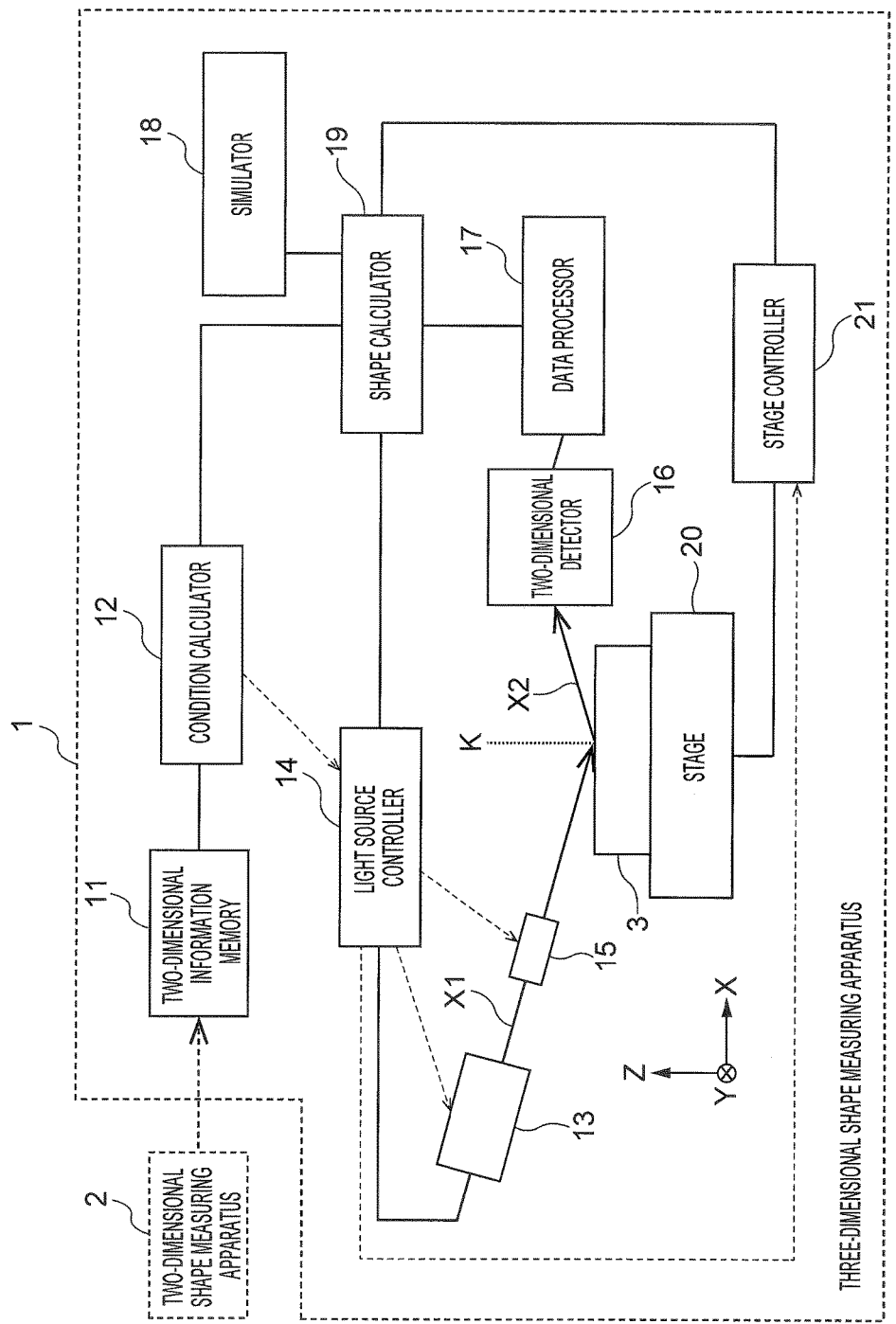
FIG. 1 is a schematic diagram illustrating a configuration of a three-dimensional shape measuring apparatus of a first embodiment.

FIG. 1 is a schematic diagram illustrating a configuration of a three-dimensional shape measuring apparatus 1 of a first embodiment.

The three-dimensional shape measuring apparatus 1 in FIG. 1 includes a two-dimensional information memory 11, a condition calculator 12, an X-ray tube bulb 13, a light source controller 14, a divergence slit 15, a two-dimensional detector 16, a data processor 17, a simulator 18, a shape calculator 19, a stage 20, and a stage controller 21. FIG. 1 further illustrates a two-dimensional shape measuring apparatus 2 and a sample 3.

Hereinafter, a detailed description of the three-dimensional shape measuring apparatus 1 is given with reference to FIG. 1. Reference to FIGS. 2 to 5 is also made, as appropriate, in this description.

The two-dimensional information memory 11 stores, as information about patterns provided in the sample 3, two-dimensional information (two-dimensional in-plane information) about a plane parallel with a surface of the sample 3. The two-dimensional information memory 11 is one example of a memory.

Examples of the sample 3 include a semiconductor wafer, an IC (integrated circuit) chip, a mask for exposure, and a nanoimprint template. In FIG. 1, an X direction and a Y direction which are parallel with the surface of the sample 3 and are orthogonal to each other, and a Z direction which is orthogonal to the surface of the sample 3 are shown. The +Z direction and the −Z direction represent herein the upward direction and the downward direction, respectively. The −Z direction may match the gravity direction or may not match the gravity direction.

Figure 2:
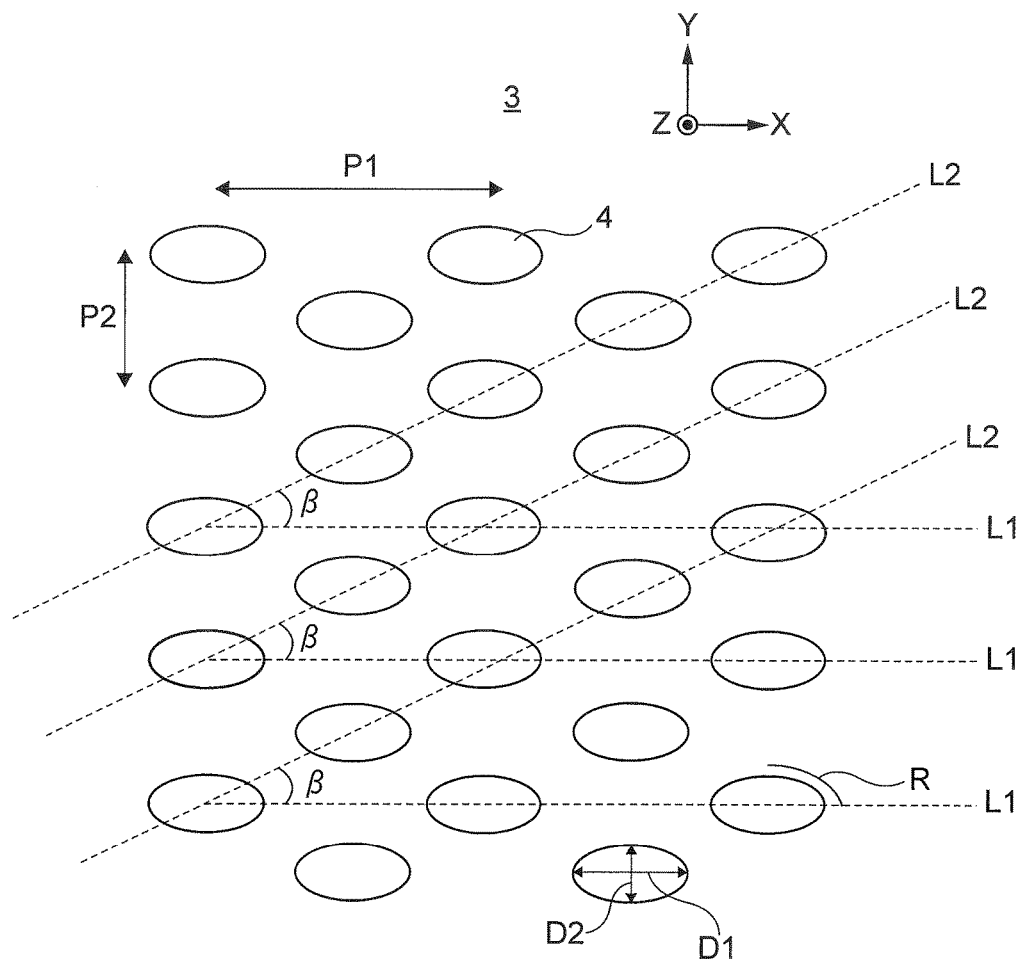
FIG. 2 is a top view of an example of patterns provided in a sample of the first embodiment.

FIG. 2 is a top view showing an example of patterns provided in the sample 3 of the first embodiment.

In FIG. 2, a plurality of two-dimensionally arranged hole patterns 4 are illustrated. Examples of the hole patterns 4 include contact holes, via holes, and memory holes. The hole patterns 4 are arranged at respective points of intersection between a plurality of first straight lines L1 extending in a first direction and a plurality of second straight lines L2 extending in a second direction. The reference characters "β" represent respective angles between the first straight lines L1 and the second straight lines L2, and 0°<β<90° is satisfied herein.

Each of the hole patterns 4 has an elliptical flat shape. In FIG. 2, a dimension D1 (a long diameter), in the X direction, of each of the hole patterns 4, a dimension D2 (a short diameter), in the Y direction, of each of the hole patterns 4, and the curvature R of each of the hole patterns 4 are shown. In FIG. 2, a pitch P1 between the hole patterns 4 in the X direction, and a pitch P2 between the hole patterns 4 in the Y direction are also shown. In the following description of the present embodiment, patterns to be measured are holes. However, a pattern to be measured may be another pattern such as a line-and-space pattern.

As described above, the two-dimensional information memory 11 stores, as information about patterns provided in the sample 3, two-dimensional information about the plane parallel with the surface of the sample 3. The two-dimensional information in the present embodiment includes information about the two-dimensional shapes of the hole patterns 4 in the surface (the XY plane) of the sample 3 and information about two-dimensional arrangement of the hole patterns 4. The former information is the dimension D1, the dimension D2, and the curvature R, for example. The latter information is the direction of each of the first straight lines L1, the direction of each of the second straight lines L2, the pitch P1, the pitch P2, and the angle β, for example.

The two-dimensional information is measured, by use of the sample 3 in FIG. 1, outside the three-dimensional shape measuring apparatus 1, and is stored in the two-dimensional information memory 11. The two-dimensional information in the present embodiment is measured by the two-dimensional shape measuring apparatus 2. Examples of the two-dimensional shape measuring apparatus 2 include an SEM (a scanning electron microscope) and a TEM (a transmission electron microscope). The two-dimensional shape measuring apparatus 2 may be an apparatus (e.g., an ion beam microscope) other than the above examples. When two-dimensional information of a wide area which cannot be measured by the two-dimensional shape measuring apparatus 2 is required, the two-dimensional information may be acquired from design data. Before shape measurement using the sample 3 is performed in the three-dimensional shape measuring apparatus 1, at least one kind (e.g., the dimension) of two-dimensional information is stored in advance in the two-dimensional information memory 11 through the two-dimensional shape measuring apparatus 2.

The description of the three-dimensional shape measuring apparatus 1 with reference to FIG. 1 is continued below.

The condition calculator 12 acquires the two-dimensional information from the two-dimensional information memory 11, and calculates a shape measurement condition in accordance with the two-dimensional information. Examples of such a condition include the incident angle of a beam with respect to the XY plane, the incident angle (the incident azimuth) of a beam within the XY plane, the wavelength of a beam, the width of a divergence slit, and a measurement time.

The X-ray tube bulb 13 generates a beam as indicated by a reference character "X1", and irradiates the surface of the sample 3 with the beam. The X-ray tube bulb 13 is one example of an irradiation module. Examples of a beam in the present embodiment include a particle beam and an electromagnetic beam. A beam herein refers to an X ray having a wavelength of 1 nm or shorter.

The light source controller 14 controls operations of the X-ray tube bulb 13, the divergence slit 15, and the stage 20, etc. in accordance with the above two-dimensional information. More specifically, the light source controller 14 receives, from the condition calculator 12, a shape measurement condition calculated from the two-dimensional information, and controls operations of the X-ray tube bulb 13 and the like in accordance with the condition. The light source controller 14 controls operations of the X-ray tube bulb 13, the stage 20, and the like in accordance with the condition calculated from the two-dimensional information by the condition calculator 12. Alternatively, when a condition cannot be calculated from the two-dimensional information, the light source controller 14 may control operations of the X-ray tube bulb 13, the stage 20, and the like by using a condition (an incident angle, an incident azimuth, the wavelength of a beam, a divergence angle, or a measurement time, etc.) prepared in advance. Each of the light source controller 14 and the condition calculator 12 is one example of an irradiation controller.

The light source controller 14 controls an irradiation direction of the beam to the sample 3, for example. The irradiation direction of the beam is the incident angle of a beam with respect to the XY plane, or the incident angle of a beam within the XY plane, for example. The former incident angle corresponds to an elevation angle for indicating the irradiation direction of the beam, and is also referred to as an elevation angle of a beam, hereinafter. The latter incident angle corresponds to an azimuth for indicating the irradiation direction of the beam, and is also referred to as an azimuth of a beam (or an incident azimuth) hereinafter.

The elevation angle of a beam is an angle between the surface of the sample 3 and an arrow denoted by a reference character "X1". The elevation angle in the present embodiment is adjusted to such an angle that causes a beam which is an X ray not to pass through the sample 3 but to be totally reflected by the surface of the sample 3. The elevation angle is 1° or smaller, for example. In this way, shape measurement using small-angle X-ray scattering is performed in the present embodiment. The light source controller 14 may set the elevation angle in accordance with the condition calculated from the two-dimensional information by the condition calculator 12, or may set the elevation angle in accordance with a condition prepared in advance. The light source controller 14 controls the elevation angle of a beam by controlling operation of the X-ray tube bulb 13.

The azimuth of a beam can be changed by rotation of the irradiation direction of the beam about a rotation axis K orthogonal to the surface of the sample 3. Regarding rotation of the irradiation direction of the beam, the azimuth of a beam may be controlled by the light source controller 14 rotating, about the rotation axis K, the stage 20 supporting the sample 3, or the azimuth of a beam may be controlled by change of the position of the X-ray tube bulb 13 or the divergence slit 15. A detailed description of a method by which the light source controller 14 controls rotation of the stage 20 is given later.

A description of the azimuth (the incident azimuth) of a beam is given below with reference to FIGS. 3A and 3B.

Figure 3A:
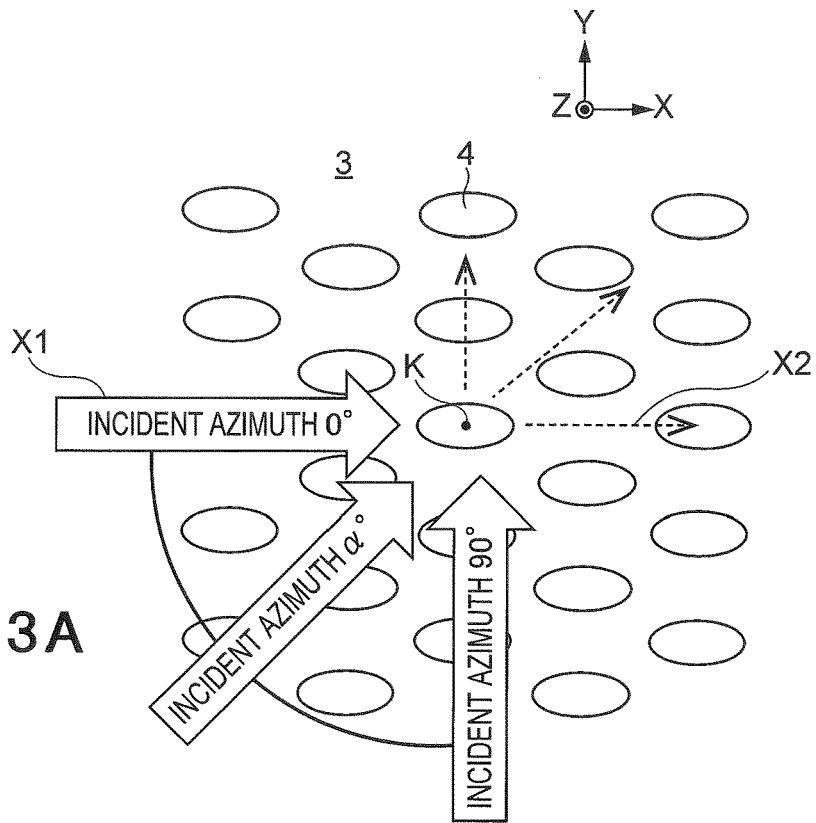
FIGS. 3A and 3B are top views of the incident azimuths of beams in the first embodiment.
Figure 3B:
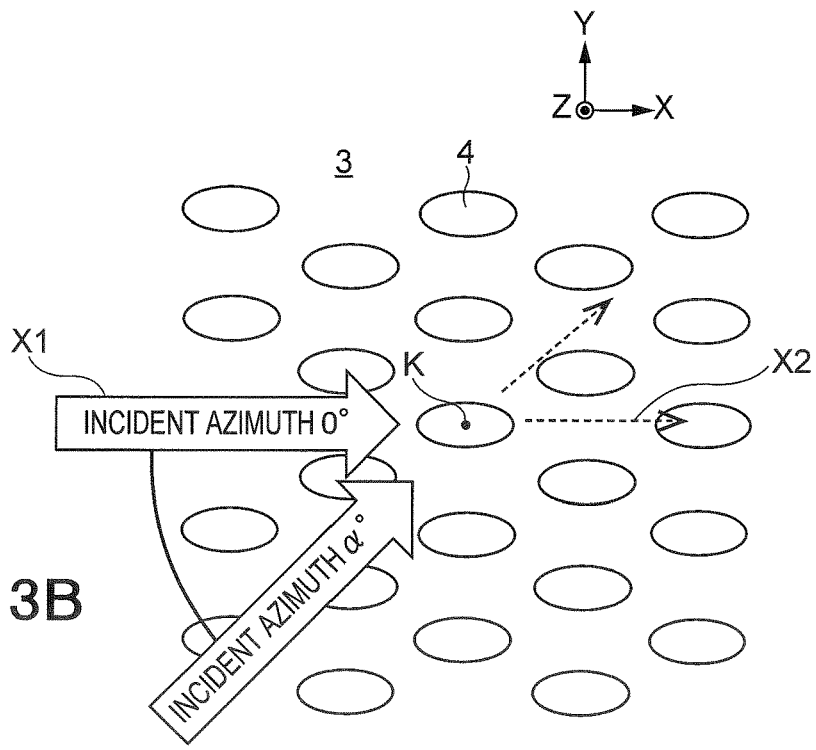

FIGS. 3A and 3B are top views of the incident azimuths of beams in the first embodiment.

FIG. 3A illustrates a state in which the hole patterns 4 in FIG. 2 are subjected to shape measurement of a modification of the present embodiment. The hole patterns 4 are arranged in a two-dimensional matrix form. In order to measure the three-dimensional shapes of the hole patterns 4, the incident azimuth of a beam needs to be changed from 0° to 90°. That is, the maximum angle range for changing the incident azimuth needs to be set to 90°.

As a result of such shape measurement, at least one of parameters such as the dimensions D1, D2, the curvature R, the pitches P1, P2, and the angle β is measured. These parameters are different from parameters such as the dimensions D1, D2, the curvature R, the pitches P1, P2, and the angle β stored as the two-dimensional information in the two-dimensional information memory 11. In addition, as a result of the shape measurement, the depth (the height) of each of the hole patterns 4, the curvature of the opening of each of the hole patterns 4 in a cross section, and the curvature of the bottom of each of the hole patterns 4 in a cross section, etc. are measured.

In the present modification, the incident azimuth of a beam is changed from 0° to 90°, whereby the three-dimensional shapes of the hole patterns 4 are measured, as described above. However, when the value of at least one of the dimensions D1, D2, the curvature R, the pitches P1, P2, and the angle β is known in advance from the two-dimensional information, a mechanism for pre-calculating the incident azimuth of a beam, etc. may be provided. Accordingly, the above shape measurement can be performed without involving change of the incident azimuth of a beam from 0° to 90°. Therefore, in the present embodiment, the above shape measurement is performed without involving change of the incident azimuth of a beam from 0° to 90°. A description of such shape measurement is given with reference to FIG. 3B.

FIG. 3B illustrates a state in which the hole patterns 4 illustrated in FIG. 2 are subjected to the shape measurement of the present embodiment when the dimensions D1, D2 are known in advance from the two-dimensional information. In the present embodiment, the incident azimuth of a beam is changed from 0° to α° in order to measure the three-dimensional shapes of the hole patterns 4. That is, the maximum angle range for changing the incident azimuth is set to α°. The condition calculator 12 acquires the value of α° from the two-dimensional information, and provides the value of α° to the light source controller 14.

As a result of this shape measurement, the measurement values of the dimension D1, the curvature R, the pitches P1, P2, and the angle β are acquired. On the other hand, the measurement value of the dimension D2 is calculated with use of the measurement value of the dimensions D1 and the values of the dimension D1 and the dimensions D2 included in the two-dimensional information. More specifically, the dimension ratio D2/D1 is calculated with use of the values of the dimensions D1, D2 included in the two-dimensional information, and the measurement value of the dimension D1 is multiplied with D2/D1, whereby the measurement value of the dimension D2 is obtained.

According to the present embodiment, the angle range of the incident azimuth can be narrowed from 90° to α° (0°<α°<90°). Accordingly, a time required for shape measurement can be shortened.

According to the present embodiment, the incident azimuth of a beam may be changed from α° to 90° such that the angle range of the incident azimuth is set to 90−α°. Contrary to the aforementioned embodiment, the measurement value of the dimension D1 in this case is calculated with use of the measurement value of the dimension D2 and the values of the dimensions D1, D2 included in the two-dimensional information.

As described above, the light source controller 14 causes the incident azimuth of a beam with respect to the sample 3 to rotate about the rotation axis K, and changes the maximum angle range for changing the incident azimuth in accordance with the two-dimensional information. Accordingly, the maximum angle range can be set to be smaller than 90 degrees.

As described later, the shape calculator 19 performs fitting of measured scattering intensity data and predicted scattering intensity data, and thereby measures the three-dimensional shapes of patterns. The shape calculator 19 performs the fitting by using not data of 90 degrees but data of a degrees which is smaller than 90 degrees. Therefore, a time required for shape measurement can be shortened.

The description of the three-dimensional shape measuring apparatus 1 with reference to FIG. 1 is continued below.

Under control by the light source controller 14, the divergence slit 15 determines a beam irradiation area on the surface of the sample 3. With the light path of a beam in the present embodiment adjusted by a convex mirror in the X-ray tube bulb 13, the beam passes through the divergence slit 15 and enters a measurement point on the sample 3 at a desired elevation angle and in a desired azimuth.

The two-dimensional detector 16 detects beams reflected (scattered) by the surface of the sample 3 as indicated by the reference character "X2", and acquires (measures) scattering intensity data about the beams. The two-dimensional detector 16 is one example of an acquisition module.

Figure 4A:
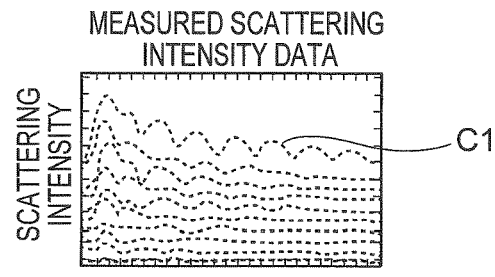
FIGS. 4A to 4E are diagrams of scattering intensity data and shape models of shape target patterns in the first embodiment.

The data processor 17 calculates scattering intensity data from scattering intensities detected by the two-dimensional detector 16. One example of the scattering intensity data is shown in FIG. 4A. FIGS. 4A to 4E are diagrams of scattering intensity data and shape models of shape target patterns in the first embodiment. The scattering intensity data in FIG. 4A shows the relationship between the scattering intensity and the exit angle of a beam reflected by the surface of the sample 3. Hereinafter, the scattering intensity data calculated by the data processor 17 is referred to as "measured scattering intensity data". The exit angle refers to an angle of a beam that is reflected (scattered) by a pattern surface.

The simulator 18 predicts and sets a shape model of a pattern provided in the sample 3, for example, without using parameters stored in the two-dimensional information memory 11, and calculates predicted beam scattering intensity data in accordance with the set shape model. The simulator 18 is one example of a calculator. The shape model refers to a model representing the three-dimensional shape of a pattern in the sample 3 by using one or more parameters. Examples of the parameters include the dimensions D1, D2, the curvature R, the depth (height) of each pattern, the pitches P1, P2 between patterns, and the curvatures, in a cross section, of the opening and the bottom of each pattern. Here, the shape of a pattern to be measured is predicted and set in advance to the possible extent. A fitting process (described later) is facilitated by setting of such a shape model.

Figure 4B:
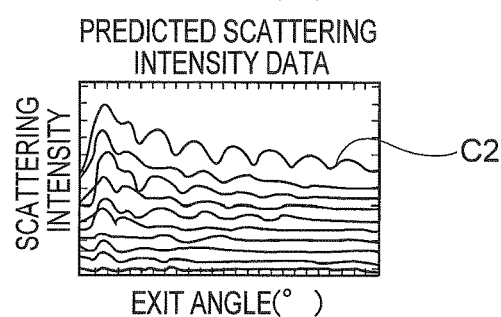

One example of the predicted scattering intensity data calculated by the simulator 18 is shown in FIG. 4B. The predicted scattering intensity data in FIG. 4B shows predicted results of the relationship between the exit angle and the scattering intensity, as indicated by a plurality of curved lines C2. FIGS. 4D and 4E each show one example of the shape model which is set by the simulator 18 for one of the hole patterns 4 provided in the sample 3.

Figure 4C:
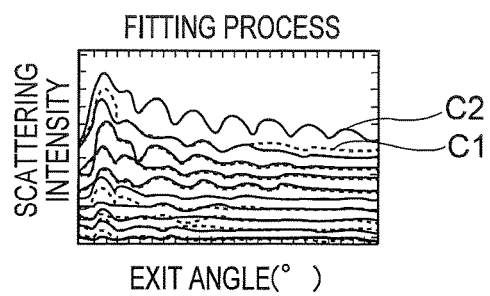
Figure 4D:
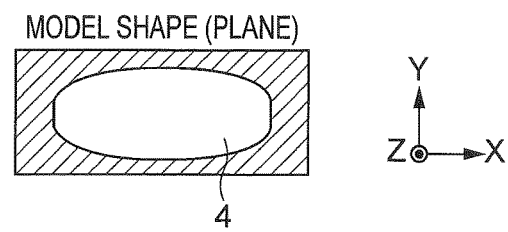
Figure 4E:
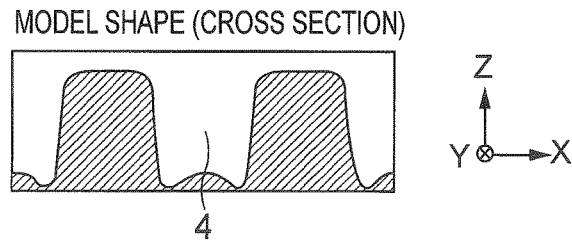

The shape calculator 19 performs fitting of the measured scattering intensity data and the predicted scattering intensity data, while adjusting one or more parameters of the shape model (FIG. 4C). For example, the shape calculator 19 varies some of the parameters of the shape model to various values (that is, causes floating of the parameters), and thereby calculates various kinds of the predicted scattering intensity data, and performs fitting of the predicted scattering intensity data to the measured scattering intensity data. Then, the shape calculator 19 determines predicted scattering intensity data most similar to the measured scattering intensity data, and outputs, as a measurement result, a three-dimensional shape corresponding to the predicted scattering intensity data. In this way, the three-dimensional shape of a pattern provided in the sample 3 is measured.

More specifically, the value of a parameter used when predicted scattering intensity data which is most similar to the measured scattering intensity data is calculated, is set as a measurement value of a dimension, the curvature, the depth, or the like of the pattern provided in the sample 3. The three-dimensional shape of a shape model in this case is set as a measurement result of the three-dimensional shape of the pattern provided in the sample 3.

During the fitting, the shape calculator 19 may vary the values of all the parameters, or the values of some of the parameters may be fixed values. The shape calculator 19 adjusts the values of the parameters in conjunction with the simulator 18, for example.

As an alternative fitting method, fitting of one set of the predicted scattering intensity data to the measured scattering intensity data is performed without variation of the values of the parameters, another set of the predicted scattering intensity data is obtained, if the parameters include unmatched one, by varying only the unmatched parameter, and fitting of the other set of the predicted scattering intensity data to the measured scattering intensity data is repeated.

Figure 5:
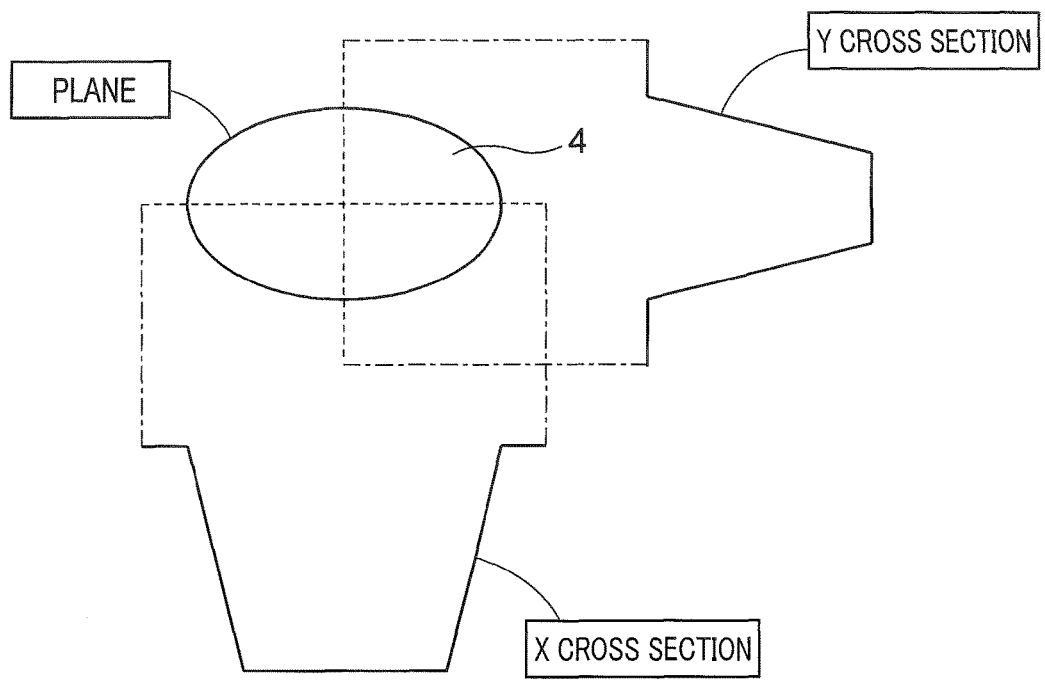
FIG. 5 is a diagram showing a result of shape measurement of the first embodiment.

FIG. 5 is a diagram showing a result of the shape measurement of the first embodiment.

In FIG. 5, the plane shape, the cross-sectional shape at an X cross section, and the cross-sectional shape at a Y cross section of each of the hole patterns 4 are shown. According to the shape measurement of the present embodiment, the cross-sectional shape of each of the hole patterns 4 at an arbitrary cross section can be measured. Each of two sectional shapes in FIG. 5 is one example of such a cross-sectional shape.

The description of the three-dimensional shape measuring apparatus 1 with reference to FIG. 1 is continued below.

The stage 20 is used such that the sample 3 is placed thereon. On the stage 20, the sample 3 is placed with a patterned surface thereof facing upward.

The stage controller 21 controls operation of the stage 20. For example, the stage controller 21 can move the stage 20 in ±X, ±Y, and ±Z directions, and can rotate the stage 20 about the rotation axis K.

When the sample 3 is irradiated with a beam, the light source controller 14 rotates the stage 20 by sending an instruction to the stage controller 21, for example. As a result, while the incident azimuth of a beam is changed, the sample 3 can be irradiated with a beam. Here, by sending an instruction to the stage controller 21, the light source controller 14 changes the incident azimuth of a beam from 0° to α°, and limits the maximum angle range for changing the incident azimuth to α°. During the irradiation with a beam, the two-dimensional detector 16 acquires a two-dimensional image obtained by integrating beam scattering intensities. The two-dimensional image is provided, as scattering intensity data, to the data processor 17. Alternatively, the incident azimuth of a beam may be changed not through rotation of the stage 20 as described above, but through controlling of the X-ray tube bulb 13 and/or the divergence slit 15.

Figure 6:
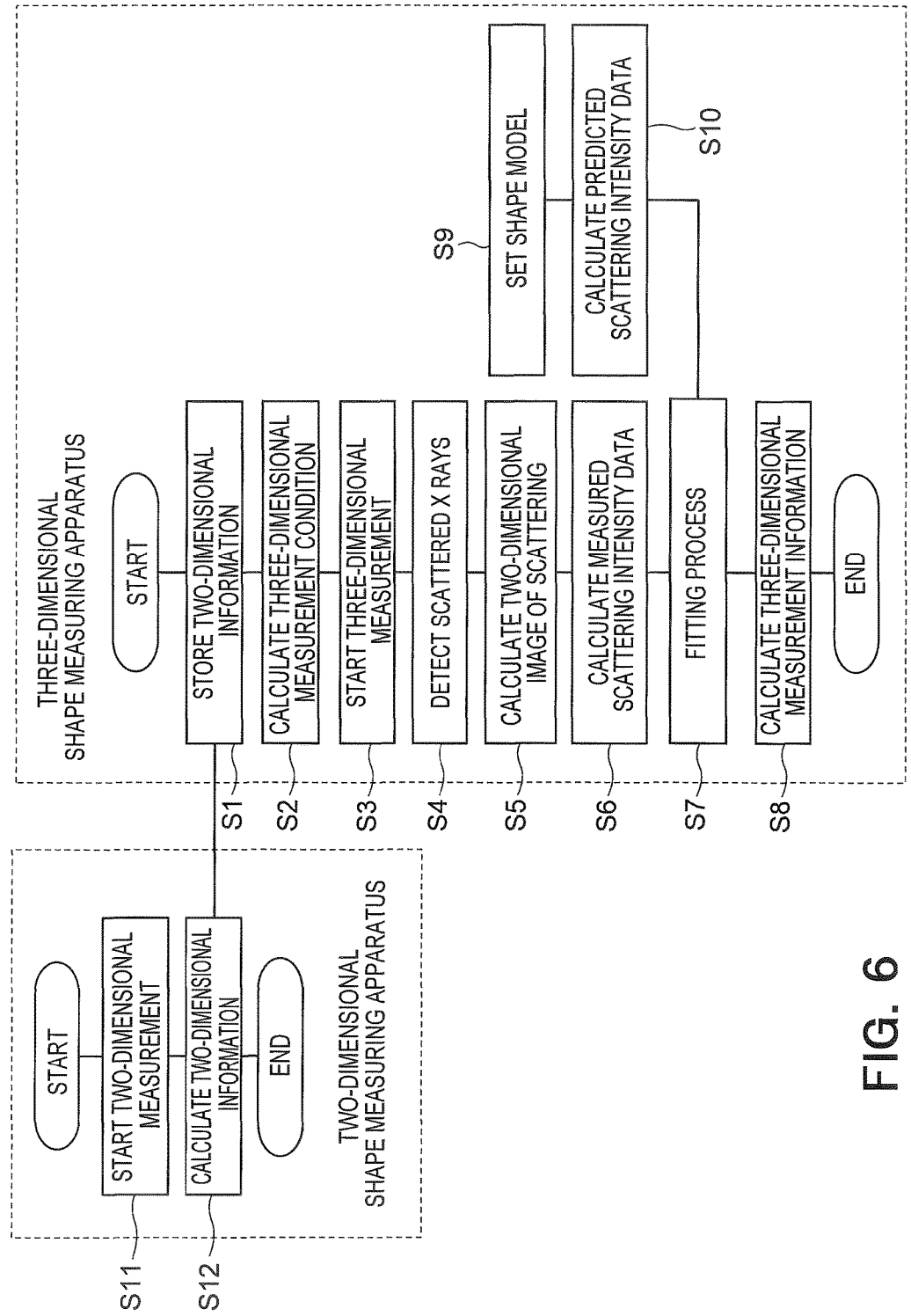
FIG. 6 is a flowchart showing operation of the three-dimensional shape measuring apparatus of the first embodiment.

FIG. 6 is a flowchart showing operation of the three-dimensional shape measuring apparatus 1 of the first embodiment.

First, the two-dimensional shape measuring apparatus 2 two-dimensionally measures the sample 3 (step S11), and acquires the two-dimensional information of the sample 3 (step S12). The acquired two-dimensional information is stored in the two-dimensional information memory 11 of the three-dimensional shape measuring apparatus 1 (step S1). The condition calculator 12 calculates a shape measurement condition in accordance with the two-dimensional information (step S2).

Meanwhile, when the sample 3 is set in the three-dimensional shape measuring apparatus 1, three-dimensional measurement of the sample 3 is started (step S3). First, the X-ray tube bulb 13 irradiates the sample 3 with an X ray (a beam), and the two-dimensional detector 16 detects X rays scattered from the sample 3 (step S4). At this time, the light source controller 14 changes the incident azimuth of the X ray to the sample 3.

Next, the two-dimensional detector 16 acquires a two-dimensional image indicating distribution of the scattering intensities of X rays, and provides the two-dimensional image to the data processor 17 (step S5). The data processor 17 calculates measured scattering intensity data from the two-dimensional image, and provides the measured scattering intensity data to the shape calculator 19 (step S6). Meanwhile, the simulator 18 sets a shape model of a pattern in the sample 3 (step S9), and calculates predicted scattering intensity data about a beam in accordance with the shape model (step S10).

Then, the shape calculator 19 performs fitting of the measured scattering intensity data and the predicted scattering intensity data, while adjusting one or more parameters of the shape model (step S7). As a result, the three-dimensional information of the pattern is calculated, and the measurement result of the three-dimensional shape is outputted (step S8). The measurement result of the three-dimensional shape may be stored in the three-dimensional shape measuring apparatus 1 or in an information processing apparatus connected thereto, or may be displayed on a monitor of the three-dimensional shape measuring apparatus 1 or on a monitor of an information processing apparatus connected thereto.

As described above, the light source controller 14 of the present embodiment controls the irradiation direction of the beam with respect to the sample 3 in accordance with the two-dimensional information about the sample 3 provided from the two-dimensional shape measuring apparatus 2. More specifically, the light source controller 14 rotates the incident azimuth of a beam with respect to the sample 3 about the rotation axis K, and sets the angle range for changing the incident azimuth in accordance with the two-dimensional information. Consequently, the angle range can be set to be smaller than 90 degrees.

According to the present embodiment, an angle range for changing the irradiation direction of the beam is narrowed so that a measurement time is shortened or the number of parameters is limited, whereby the measurement accuracy can be enhanced. Consequently, according to the embodiment, the three-dimensional shape of a pattern provided in the sample 3 can be preferably measured with high accuracy in a short time, for example.

While certain embodiments have been described, these embodiments have been presented by way of example only, and are not intended to limit the scope of the inventions. Indeed, the novel apparatuses and methods described herein may be embodied in a variety of other forms; furthermore, various omissions, substitutions and changes in the form of the apparatuses and methods described herein may be made without departing from the spirit of the inventions. The accompanying claims and their equivalents are intended to cover such forms or modifications as would fall within the scope and spirit of the inventions.

The invention claimed is:

1. A shape measuring apparatus comprising:
a memory configured to store, as information regarding a pattern provided in a sample, two-dimensional information regarding a plane parallel with a surface of the sample;
an irradiation module configured to irradiate the surface of the sample with a beam;
an irradiation controller configured to control an irradiation direction of the beam to the sample in accordance with the two-dimensional information;
a detector configured to detect the beam reflected by the surface of the sample to acquire scattering intensity data regarding the detected beam;
a calculator configured to calculate predicted scattering intensity data regarding the beam in accordance with a shape model that represents a three-dimensional shape of the pattern with use of a parameter; and a fitting processor configured to fit the scattering intensity data and the predicted scattering intensity data by adjusting the parameter of the shape model to measure the three-dimensional shape of the pattern.

2. The apparatus of claim 1, wherein the irradiation controller rotates the irradiation direction of the beam about a rotation axis orthogonal to the surface of the sample, and sets an angle range for changing the irradiation direction in accordance with the two-dimensional information.

3. The apparatus of claim 2, wherein the irradiation controller sets the angle range to be smaller than 90 degrees.

4. The apparatus of claim 2, wherein the irradiation controller further controls an elevation angle of the beam with respect to the sample.

5. The apparatus of claim 4, wherein the irradiation controller controls the elevation angle such that the beam is totally reflected by the surface of the sample.

6. The apparatus of claim 4, wherein the irradiation controller controls the elevation angle to be 1° or smaller.

7. The apparatus of claim 1, wherein the two-dimensional information includes information regarding a two-dimensional shape of each pattern in the plane parallel with the surface of the sample, or information regarding two-dimensional arrangement of patterns in the plane parallel with the surface of the sample.

8. The apparatus of claim 7, wherein the two-dimensional information includes dimensions, in two directions, of each pattern in the plane parallel with the surface of the sample.

9. The apparatus of claim 7, wherein the two-dimensional information includes a curvature of each pattern in the plane parallel with the surface of the sample.

10. The apparatus of claim 7, wherein the two-dimensional information includes pitches, in two directions, between the patterns in the plane parallel with the surface of the sample.

11. The apparatus of claim 1, wherein the two-dimensional information is measured outside the shape measuring apparatus.

12. The apparatus of claim 11, wherein the two-dimensional information is measured by a scanning electron microscope (SEM) or a transmission electron microscope (TEM) provided outside the shape measuring apparatus.

13. The apparatus of claim 1, wherein the irradiation module irradiates the surface of the sample with the beam that is a particle beam or an electromagnetic beam.

14. The apparatus of claim 13, wherein the irradiation module irradiates the surface of the sample with an X ray having a wavelength of 1 nm or shorter.

15. A shape measuring method comprising:
acquiring, as information regarding a pattern provided in a sample, two-dimensional information regarding a plane parallel with a surface of the sample;
irradiating the surface of the sample with a beam;
controlling an irradiation direction of the beam to the sample in accordance with the two-dimensional information;
acquiring scattering intensity data regarding the beam reflected by the surface of the sample;
calculating predicted scattering intensity data regarding the beam in accordance with a shape model that represents a three-dimensional shape of the pattern with use of a parameter; and
measuring the three-dimensional shape of the pattern by adjusting the parameter of the shape model and fitting the scattering intensity data and the predicted scattering intensity data.

16. The method of claim 15, wherein the controlling of the irradiation direction of the beam to the sample includes rotating the irradiation direction of the beam about a rotation axis orthogonal to the surface of the sample, and setting an angle range for changing the irradiation direction in accordance with the two-dimensional information.

17. The method of claim 16, wherein the controlling of the irradiation direction of the beam to the sample includes setting the angle range to be smaller than 90 degrees.

18. The method of claim 15, wherein the two-dimensional information includes information regarding a two-dimensional shape of each pattern in the plane parallel with the surface of the sample, or information regarding two-dimensional arrangement of patterns in the plane parallel with the surface of the sample.

19. The method of claim 18, wherein the two-dimensional information includes dimensions, in two directions, of each pattern in the plane parallel with the surface of the sample.

20. The method of claim 18, wherein the two-dimensional information includes pitches, in two directions, between the patterns in the plane parallel with the surface of the sample.

* * * * *